(12) United States Patent
Chen et al.

(10) Patent No.: US 11,286,475 B2
(45) Date of Patent: Mar. 29, 2022

(54) **TYROSOL-PRODUCING RECOMBINANT *ESCHERICHIA COLI* AND CONSTRUCTION METHOD AND APPLICATION THEREOF**

(71) Applicant: Jiangnan University, Wuxi (CN)

(72) Inventors: Xianzhong Chen, Wuxi (CN); Wei Xu, Wuxi (CN); Wei Shen, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/134,633

(22) Filed: Dec. 28, 2020

(65) Prior Publication Data
US 2021/0115429 A1    Apr. 22, 2021

Related U.S. Application Data

(63) Continuation of application No. PCT/CN2019/012014, filed on Nov. 22, 2019.

(30) Foreign Application Priority Data

Aug. 15, 2019    (CN) .......................... 2019107544979

(51) Int. Cl.
| | |
|---|---|
| *C12N 9/88* | (2006.01) |
| *C12P 7/22* | (2006.01) |
| *C12N 15/90* | (2006.01) |
| *C12N 15/11* | (2006.01) |
| *C12N 9/22* | (2006.01) |

(52) U.S. Cl.
CPC ................. *C12N 9/88* (2013.01); *C12N 9/22* (2013.01); *C12N 15/11* (2013.01); *C12N 15/902* (2013.01); *C12P 7/22* (2013.01); *C12Y 401/01001* (2013.01); *C12N 2310/20* (2017.05); *C12N 2800/80* (2013.01)

(58) Field of Classification Search
CPC . C12N 9/88; C12N 15/11; C12N 9/22; C12N 15/902; C12N 2800/80; C12N 2310/20; C12Y 401/01001; C12P 7/22
See application file for complete search history.

(56) References Cited

FOREIGN PATENT DOCUMENTS

| | | |
|---|---|---|
| CN | 104099379 A | 10/2014 |
| CN | 104946575 A | 9/2015 |
| CN | 106566794 A | 4/2017 |
| CN | 106754607 A | 5/2017 |
| CN | 107435049 A | 12/2017 |
| CN | 110452865 A | 11/2019 |
| WO | 2011088425 A2 | 7/2011 |

OTHER PUBLICATIONS

Bai et al., Scientific Reports 4:6640, pp. 1-8, published Oct. 17, 2014.*

* cited by examiner

*Primary Examiner* — Delia M Ramirez
(74) *Attorney, Agent, or Firm* — IPRO, PLLC; Na Xu

(57) ABSTRACT

The disclosure relates to a tyrosol-producing recombinant *Escherichia coli* and a construction method and application thereof and belongs to the technical field of bioengineering. The *Escherichia coli* undergoes heterologous expression of a codon-optimized *Saccharomyces cerevisiae* pyruvate decarboxylase gene ARO10*. According to the recombinant *Escherichia coli*, five sites of a lacI site, a trpE site, a pabB site, a pabA site and a pykF site of an *Escherichia coli* genome are deleted, and at the same time, the ARO10* gene is integrated at each site of the five sites to obtain a strain containing multiple copies of the ARO10* gene. On the basis of the above recombinant strain, the ARO10* gene is randomly integrated at multiple sites, and it is found that a strain with high-yield production of tyrosol can be obtained by inserting the ARO10* gene at a yccX site. Fermentation using this strain does not require inducers or antibiotics. After fermentation is carried out for 48 hours, the yield of tyrosol can reach 32.3 mM.

13 Claims, 3 Drawing Sheets
Specification includes a Sequence Listing.

SEQUENCE LISTING

<160> NUMBER OF SEQ ID NOS: 66

<210> SEQ ID NO 1
<211> LENGTH: 1908
<212> TYPE: DNA
<213> ORGANISM: Artificial sequence
<220> FEATURE:
<223> OTHER INFORMATION: Synthetic DNA

<400> SEQUENCE: 1

| | | | | | |
|---|---|---|---|---|---|
| atggctccgg | ttaccatcga | aaaattcgtt | aaccaggaag | aacgtcacct | ggtttctaac | 60 |
| cgttctgcta | ccatcccgtt | cggtgaatac | atcttcaaac | gtctgctgtc | tatcgacacc | 120 |
| aaatctgttt | tcggtgttcc | gggtgacttc | aacctgtctc | tgctggaata | cctgtactct | 180 |
| ccgtctgttg | aatctgctgg | tctgcgttgg | gttggtacct | gcaacgaact | gaacgctgct | 240 |
| tacgctgctg | acggttactc | tcgttactct | aacaaaatcg | ttgcctgat | caccacctac | 300 |
| ggtgttggtg | aactgtctgc | tctgaacggt | atcgctggtt | ctttcgctga | aaacgttaaa | 360 |
| gttctgcaca | tcgttggtgt | tgctaaatct | atcgactctc | gttcttctaa | cttctctgac | 420 |
| cgtaacctgc | accacctggt | tccgcagctg | cacgactcta | acttcaaagg | tccgaaccac | 480 |
| aaagtttacc | acgacatggt | taaagaccgt | gttgcttgct | ctgttgctta | cctggaagac | 540 |
| atcgaaaccg | cttgcgacca | ggttgacaac | gttatccgtg | acatctacaa | atactctaaa | 600 |
| ccgggttaca | tcttcgttcc | ggctgacttc | gctgacatgt | ctgttacctg | cgacaacctg | 660 |
| gttaacgttc | cgcgtatctc | tcagcaggac | tgcatcgttt | acccgtctga | aaaccagctg | 720 |
| tctgacatca | tcaacaaaat | cacctcttgg | atctactctt | ctaaaacccc | ggctatcctg | 780 |
| ggtgactttt | taaccgaccg | ttacggtgta | agcaacttcc | tgaacaaaact | gatctgcaaa | 840 |
| accggtatct | ggaacttctc | taccgttatg | ggtaaatctg | ttatcgacga | atctaacccg | 900 |
| acctacatgg | gtcagtacaa | cggtaaagaa | ggtctgaaac | aggtttacga | acacttcgaa | 960 |
| ctgtgcgacc | tggttctgca | cttcggtgtt | gacatcaacg | aaatcaacaa | cggtcactac | 1020 |
| accttcacct | acaaaccgaa | cgctaaaatc | atccagttcc | acccgaacta | catccgtctg | 1080 |
| gttgacaccc | gtcagggtaa | cgaacagatg | ttcaaaggta | tcaacttcgc | tccgatcctg | 1140 |
| aaagaactgt | acaaacgtat | cgacgtttct | aaactgtctc | tgcagtacga | ctctaacgtt | 1200 |
| acccagtaca | ccaacgaaac | catgcgtctg | gaagacccga | ccaacggtca | gtcttctatc | 1260 |
| atcacccagg | ttcacctgca | gaaaaccatg | ccgaaattcc | tgaacccggg | tgacgttgtt | 1320 |
| gtttgcgaaa | ccggttcttt | ccagttctct | gttcgtgact | cgctttccc | gtctcagctg | 1380 |
| aaatacatct | ctcagggttt | cttcctgtct | atcggtatgg | ctctgccggc | tgctctgggt | 1440 |
| gttggtatcg | ctatgcagga | ccactctaac | gctcacatca | acggtggtaa | cgttaaagaa | 1500 |
| gactacaaac | cgcgtctgat | cctgttcgaa | ggtgacggtg | ctgctcagat | gaccatccag | 1560 |
| gaactgtcta | ccatcctgaa | atgcaacatc | ccgctggaag | ttatcatctg | gaacaacaac | 1620 |
| ggttacacca | tcgaacgtgc | tatcatgggt | ccgacccgtt | cttacaacga | cgttatgtct | 1680 |
| tggaaatgga | ccaaactgtt | cgaagcgttc | ggtgacttcg | acggtaaata | caccaactct | 1740 |
| accctgatcc | agtgcccgtc | taaactggct | ctgaaactgg | aagaactgaa | aaactctaac | 1800 |
| aaacgttctg | tatcgaact | gctggaagtt | aaactgggtg | aactggactt | cccggaacag | 1860 |
| ctgaaatgca | tggttgaagc | tgctgctctg | aaacgtaaca | aaaaataa | | 1908 |

<210> SEQ ID NO 2
<211> LENGTH: 29

```
<212> TYPE: DNA
<213> ORGANISM: Artificial sequence
<220> FEATURE:
<223> OTHER INFORMATION: Synthetic DNA

<400> SEQUENCE: 2
ggctcgagat ggctgtgcag gtcgtaaat                                       29

<210> SEQ ID NO 3
<211> LENGTH: 134
<212> TYPE: DNA
<213> ORGANISM: Artificial sequence
<220> FEATURE:
<223> OTHER INFORMATION: Synthetic DNA

<400> SEQUENCE: 3
ggggtaccgt gaaaccagta acgttatacg atgtcgcaga gttcatcact gcccgctttc     60
cagtcgggaa acctgtcgtg ccagctgcat taatgaatcg gccaacgcgc ggggagaaga    120
gtttgtagaa acgc                                                      134

<210> SEQ ID NO 4
<211> LENGTH: 89
<212> TYPE: DNA
<213> ORGANISM: Artificial sequence
<220> FEATURE:
<223> OTHER INFORMATION: Synthetic DNA

<400> SEQUENCE: 4
ccctcgaggt gaaaccagta acgttatacg atgtcgcaga gtatgccggt gtctcttatc     60
agaccgtttg tgtaggctgg agctgcttc                                       89

<210> SEQ ID NO 5
<211> LENGTH: 28
<212> TYPE: DNA
<213> ORGANISM: Artificial sequence
<220> FEATURE:
<223> OTHER INFORMATION: Synthetic DNA

<400> SEQUENCE: 5
ccctcgagat tccggggatc cgtcgacc                                        28

<210> SEQ ID NO 6
<211> LENGTH: 20
<212> TYPE: DNA
<213> ORGANISM: Artificial sequence
<220> FEATURE:
<223> OTHER INFORMATION: Synthetic DNA

<400> SEQUENCE: 6
gaagcggcat gcatttacgt                                                 20

<210> SEQ ID NO 7
<211> LENGTH: 20
<212> TYPE: DNA
<213> ORGANISM: Artificial sequence
<220> FEATURE:
<223> OTHER INFORMATION: Synthetic DNA

<400> SEQUENCE: 7
acaacatacg agccggaagc                                                 20

<210> SEQ ID NO 8
<211> LENGTH: 28
<212> TYPE: DNA
```

```
<213> ORGANISM: Artificial sequence
<220> FEATURE:
<223> OTHER INFORMATION: Synthetic DNA

<400> SEQUENCE: 8
cggactagta ttatacctag gactgagc                                        28

<210> SEQ ID NO 9
<211> LENGTH: 49
<212> TYPE: DNA
<213> ORGANISM: Artificial sequence
<220> FEATURE:
<223> OTHER INFORMATION: Synthetic DNA

<400> SEQUENCE: 9
cggactagtc ctgttctctt atgaccttgg ttttagagct agaaatagc                 49

<210> SEQ ID NO 10
<211> LENGTH: 20
<212> TYPE: DNA
<213> ORGANISM: Artificial sequence
<220> FEATURE:
<223> OTHER INFORMATION: Synthetic DNA

<400> SEQUENCE: 10
cctgttctct tatgaccttg                                                 20

<210> SEQ ID NO 11
<211> LENGTH: 54
<212> TYPE: DNA
<213> ORGANISM: Artificial sequence
<220> FEATURE:
<223> OTHER INFORMATION: Synthetic DNA

<400> SEQUENCE: 11
gagtcggtgc ttttttgaa ttctctagac caggtatttg cgcttttca agtc             54

<210> SEQ ID NO 12
<211> LENGTH: 43
<212> TYPE: DNA
<213> ORGANISM: Artificial sequence
<220> FEATURE:
<223> OTHER INFORMATION: Synthetic DNA

<400> SEQUENCE: 12
atttacgacc tgcacagcca tcgggctggg tatctgattg ctt                       43

<210> SEQ ID NO 13
<211> LENGTH: 43
<212> TYPE: DNA
<213> ORGANISM: Artificial sequence
<220> FEATURE:
<223> OTHER INFORMATION: Synthetic DNA

<400> SEQUENCE: 13
aagcaatcag atacccagcc cgatggctgt gcaggtcgta aat                       43

<210> SEQ ID NO 14
<211> LENGTH: 47
<212> TYPE: DNA
<213> ORGANISM: Artificial sequence
<220> FEATURE:
<223> OTHER INFORMATION: Synthetic DNA

<400> SEQUENCE: 14
gaatgtcagc catcagaaag tctccgtttg tagaaacgca aaaggc                    47
```

<210> SEQ ID NO 15
<211> LENGTH: 47
<212> TYPE: DNA
<213> ORGANISM: Artificial sequence
<220> FEATURE:
<223> OTHER INFORMATION: Synthetic DNA

<400> SEQUENCE: 15
gcctttttgc gtttctacaa acggagactt tctgatggct gacattc             47

<210> SEQ ID NO 16
<211> LENGTH: 53
<212> TYPE: DNA
<213> ORGANISM: Artificial sequence
<220> FEATURE:
<223> OTHER INFORMATION: Synthetic DNA

<400> SEQUENCE: 16
ggtaatagat ctaagcttct gcaggtcgac gctgaaaaca gctggtggct ttc       53

<210> SEQ ID NO 17
<211> LENGTH: 22
<212> TYPE: DNA
<213> ORGANISM: Artificial sequence
<220> FEATURE:
<223> OTHER INFORMATION: Synthetic DNA

<400> SEQUENCE: 17
ccagaccgtg gaaatttcca cg                                         22

<210> SEQ ID NO 18
<211> LENGTH: 25
<212> TYPE: DNA
<213> ORGANISM: Artificial sequence
<220> FEATURE:
<223> OTHER INFORMATION: Synthetic DNA

<400> SEQUENCE: 18
gagaatggat tccggatgga actgg                                      25

<210> SEQ ID NO 19
<211> LENGTH: 47
<212> TYPE: DNA
<213> ORGANISM: Artificial sequence
<220> FEATURE:
<223> OTHER INFORMATION: Synthetic DNA

<400> SEQUENCE: 19
gaatgtcagc catcagaaag tctcccgggc tgggtatctg attgctt              47

<210> SEQ ID NO 20
<211> LENGTH: 47
<212> TYPE: DNA
<213> ORGANISM: Artificial sequence
<220> FEATURE:
<223> OTHER INFORMATION: Synthetic DNA

<400> SEQUENCE: 20
aagcaatcag atacccagcc cgggagactt tctgatggct gacattc              47

<210> SEQ ID NO 21
<211> LENGTH: 60
<212> TYPE: DNA
<213> ORGANISM: Artificial sequence
<220> FEATURE:

<223> OTHER INFORMATION: Synthetic DNA

<400> SEQUENCE: 21
gtcctaggta taatactagt taaccggggc tccgaaagta gttttagagc tagaaatagc    60

<210> SEQ ID NO 22
<211> LENGTH: 20
<212> TYPE: DNA
<213> ORGANISM: Artificial sequence
<220> FEATURE:
<223> OTHER INFORMATION: Synthetic DNA

<400> SEQUENCE: 22
taaccggggc tccgaaagta    20

<210> SEQ ID NO 23
<211> LENGTH: 49
<212> TYPE: DNA
<213> ORGANISM: Artificial sequence
<220> FEATURE:
<223> OTHER INFORMATION: Synthetic DNA

<400> SEQUENCE: 23
gagtcggtgc ttttttgaa ttctctagac cctggatttc attggtgcc    49

<210> SEQ ID NO 24
<211> LENGTH: 46
<212> TYPE: DNA
<213> ORGANISM: Artificial sequence
<220> FEATURE:
<223> OTHER INFORMATION: Synthetic DNA

<400> SEQUENCE: 24
atttacgacc tgcacagcca tcagtcctga ctctactggc tatgtg    46

<210> SEQ ID NO 25
<211> LENGTH: 46
<212> TYPE: DNA
<213> ORGANISM: Artificial sequence
<220> FEATURE:
<223> OTHER INFORMATION: Synthetic DNA

<400> SEQUENCE: 25
cacatagcca gtagagtcag gactgatggc tgtgcaggtc gtaaat    46

<210> SEQ ID NO 26
<211> LENGTH: 42
<212> TYPE: DNA
<213> ORGANISM: Artificial sequence
<220> FEATURE:
<223> OTHER INFORMATION: Synthetic DNA

<400> SEQUENCE: 26
aggctacggt attccacgtc gtttgtagaa acgcaaaaag gc    42

<210> SEQ ID NO 27
<211> LENGTH: 42
<212> TYPE: DNA
<213> ORGANISM: Artificial sequence
<220> FEATURE:
<223> OTHER INFORMATION: Synthetic DNA

<400> SEQUENCE: 27 gccttttgc gtttctacaa acgacgtgga ataccgtagc ct    42

```
<210> SEQ ID NO 28
<211> LENGTH: 50
<212> TYPE: DNA
<213> ORGANISM: Artificial sequence
<220> FEATURE:
<223> OTHER INFORMATION: Synthetic DNA

<400> SEQUENCE: 28
ggtaatagat ctaagcttct gcaggtcgac cacgaattat gcctgcggtc          50

<210> SEQ ID NO 29
<211> LENGTH: 22
<212> TYPE: DNA
<213> ORGANISM: Artificial sequence
<220> FEATURE:
<223> OTHER INFORMATION: Synthetic DNA

<400> SEQUENCE: 29
gcctgctgta atagataaag cc                                        22

<210> SEQ ID NO 30
<211> LENGTH: 22
<212> TYPE: DNA
<213> ORGANISM: Artificial sequence
<220> FEATURE:
<223> OTHER INFORMATION: Synthetic DNA

<400> SEQUENCE: 30
ggcgactggc ttaactattc ac                                        22

<210> SEQ ID NO 31
<211> LENGTH: 44
<212> TYPE: DNA
<213> ORGANISM: Artificial sequence
<220> FEATURE:
<223> OTHER INFORMATION: Synthetic DNA

<400> SEQUENCE: 31
caggctacgg tattccacgt ccagtcctga ctctactggc tatg                44

<210> SEQ ID NO 32
<211> LENGTH: 44
<212> TYPE: DNA
<213> ORGANISM: Artificial sequence
<220> FEATURE:
<223> OTHER INFORMATION: Synthetic DNA

<400> SEQUENCE: 32
catagccagt agagtcagga ctggacgtgg aataccgtag cctg                44

<210> SEQ ID NO 33
<211> LENGTH: 60
<212> TYPE: DNA
<213> ORGANISM: Artificial sequence
<220> FEATURE:
<223> OTHER INFORMATION: Synthetic DNA

<400> SEQUENCE: 33
gtcctaggta taatactagt acgttattcg ccactatgcc gttttagagc tagaaatagc   60

<210> SEQ ID NO 34
<211> LENGTH: 20
<212> TYPE: DNA
<213> ORGANISM: Artificial sequence
<220> FEATURE:
<223> OTHER INFORMATION: Synthetic DNA
```

<400> SEQUENCE: 34
acgttattcg ccactatgcc                                         20

<210> SEQ ID NO 35
<211> LENGTH: 53
<212> TYPE: DNA
<213> ORGANISM: Artificial sequence
<220> FEATURE:
<223> OTHER INFORMATION: Synthetic DNA

<400> SEQUENCE: 35
gagtcggtgc tttttttgaa ttctctagag cctttagtca ctcttactgc cgc    53

<210> SEQ ID NO 36
<211> LENGTH: 43
<212> TYPE: DNA
<213> ORGANISM: Artificial sequence
<220> FEATURE:
<223> OTHER INFORMATION: Synthetic DNA

<400> SEQUENCE: 36
atttacgacc tgcacagcca tgcggctcc ggtacaaaag aac                43

<210> SEQ ID NO 37
<211> LENGTH: 43
<212> TYPE: DNA
<213> ORGANISM: Artificial sequence
<220> FEATURE:
<223> OTHER INFORMATION: Synthetic DNA

<400> SEQUENCE: 37
gttcttttgt accggagccg ccatggctgt gcaggtcgta aat               43

<210> SEQ ID NO 38
<211> LENGTH: 44
<212> TYPE: DNA
<213> ORGANISM: Artificial sequence
<220> FEATURE:
<223> OTHER INFORMATION: Synthetic DNA

<400> SEQUENCE: 38
gatcaccctg ttacgcataa acgtttgtag aaacgcaaaa aggc              44

<210> SEQ ID NO 39
<211> LENGTH: 44
<212> TYPE: DNA
<213> ORGANISM: Artificial sequence
<220> FEATURE:
<223> OTHER INFORMATION: Synthetic DNA

<400> SEQUENCE: 39
gcctttttgc gtttctacaa acgtttatgc gtaacagggt gatc              44

<210> SEQ ID NO 40
<211> LENGTH: 49
<212> TYPE: DNA
<213> ORGANISM: Artificial sequence
<220> FEATURE:
<223> OTHER INFORMATION: Synthetic DNA

<400> SEQUENCE: 40
ggtaatagat ctaagcttct gcaggtcgac tggatcggct caaccacca         49

<210> SEQ ID NO 41
<211> LENGTH: 20

<212> TYPE: DNA
<213> ORGANISM: Artificial sequence
<220> FEATURE:
<223> OTHER INFORMATION: Synthetic DNA

<400> SEQUENCE: 41
gaccattgag cttggtccgc                                                  20

<210> SEQ ID NO 42
<211> LENGTH: 21
<212> TYPE: DNA
<213> ORGANISM: Artificial sequence
<220> FEATURE:
<223> OTHER INFORMATION: Synthetic DNA

<400> SEQUENCE: 42
ccacccaccg aaacggtaaa c                                                21

<210> SEQ ID NO 43
<211> LENGTH: 44
<212> TYPE: DNA
<213> ORGANISM: Artificial sequence
<220> FEATURE:
<223> OTHER INFORMATION: Synthetic DNA

<400> SEQUENCE: 43
gatcaccctg ttacgcataa acggcggctc cggtacaaaa gaac                       44

<210> SEQ ID NO 44
<211> LENGTH: 44
<212> TYPE: DNA
<213> ORGANISM: Artificial sequence
<220> FEATURE:
<223> OTHER INFORMATION: Synthetic DNA

<400> SEQUENCE: 44
gttcttttgt accggagccg ccgtttatgc gtaacagggt gatc                       44

<210> SEQ ID NO 45
<211> LENGTH: 60
<212> TYPE: DNA
<213> ORGANISM: Artificial sequence
<220> FEATURE:
<223> OTHER INFORMATION: Synthetic DNA

<400> SEQUENCE: 45
gtcctaggta taatactagt atggttgcgg taacgtatga gttttagagc tagaaatagc      60

<210> SEQ ID NO 46
<211> LENGTH: 20
<212> TYPE: DNA
<213> ORGANISM: Artificial sequence
<220> FEATURE:
<223> OTHER INFORMATION: Synthetic DNA

<400> SEQUENCE: 46
atggttgcgg taacgtatga                                                  20

<210> SEQ ID NO 47
<211> LENGTH: 52
<212> TYPE: DNA
<213> ORGANISM: Artificial sequence
<220> FEATURE:
<223> OTHER INFORMATION: Synthetic DNA

<400> SEQUENCE: 47

```
gagtcggtgc ttttttttgaa ttctctagag gctaatgctg tacgtaatac gc         52
```

<210> SEQ ID NO 48
<211> LENGTH: 42
<212> TYPE: DNA
<213> ORGANISM: Artificial sequence
<220> FEATURE:
<223> OTHER INFORMATION: Synthetic DNA

<400> SEQUENCE: 48

```
atttacgacc tgcacagcca tgttgagaag gatgggagaa ac                     42
```

<210> SEQ ID NO 49
<211> LENGTH: 42
<212> TYPE: DNA
<213> ORGANISM: Artificial sequence
<220> FEATURE:
<223> OTHER INFORMATION: Synthetic DNA

<400> SEQUENCE: 49

```
gtttctccca tccttctcaa catggctgtg caggtcgtaa at                     42
```

<210> SEQ ID NO 50
<211> LENGTH: 43
<212> TYPE: DNA
<213> ORGANISM: Artificial sequence
<220> FEATURE:
<223> OTHER INFORMATION: Synthetic DNA

<400> SEQUENCE: 50

```
catcagggcg cttcgatata cgtttgtaga aacgcaaaaa ggc                    43
```

<210> SEQ ID NO 51
<211> LENGTH: 43
<212> TYPE: DNA
<213> ORGANISM: Artificial sequence
<220> FEATURE:
<223> OTHER INFORMATION: Synthetic DNA

<400> SEQUENCE: 51

```
gccttttgc gtttctacaa acgtatatcg aagcgccctg atg                     43
```

<210> SEQ ID NO 52
<211> LENGTH: 50
<212> TYPE: DNA
<213> ORGANISM: Artificial sequence
<220> FEATURE:
<223> OTHER INFORMATION: Synthetic DNA

<400> SEQUENCE: 52

```
ggtaatagat ctaagcttct gcaggtcgac cagcaatgcg ccttcagtag             50
```

<210> SEQ ID NO 53
<211> LENGTH: 23
<212> TYPE: DNA
<213> ORGANISM: Artificial sequence
<220> FEATURE:
<223> OTHER INFORMATION: Synthetic DNA

<400> SEQUENCE: 53

```
ctgcacattt ctcggtacag ttc                                          23
```

<210> SEQ ID NO 54
<211> LENGTH: 19
<212> TYPE: DNA
<213> ORGANISM: Artificial sequence
<220> FEATURE:
<223> OTHER INFORMATION: Synthetic DNA

<400> SEQUENCE: 54
cgcacaatgt gcgccattt                                                    19

<210> SEQ ID NO 55
<211> LENGTH: 42
<212> TYPE: DNA
<213> ORGANISM: Artificial sequence
<220> FEATURE:
<223> OTHER INFORMATION: Synthetic DNA

<400> SEQUENCE: 55
gtttctccca tccttctcaa cgtatatcga agcgccctga tg                           42

<210> SEQ ID NO 56
<211> LENGTH: 42
<212> TYPE: DNA
<213> ORGANISM: Artificial sequence
<220> FEATURE:
<223> OTHER INFORMATION: Synthetic DNA

<400> SEQUENCE: 56
catcagggcg cttcgatata cgttgagaag gatgggagaa ac                           42

<210> SEQ ID NO 57
<211> LENGTH: 60
<212> TYPE: DNA
<213> ORGANISM: Artificial sequence
<220> FEATURE:
<223> OTHER INFORMATION: Synthetic DNA

<400> SEQUENCE: 57
gtcctaggta taatactagt gaaagtctgc ataattgcct gttttagagc tagaaatagc        60

<210> SEQ ID NO 58
<211> LENGTH: 20
<212> TYPE: DNA
<213> ORGANISM: Artificial sequence
<220> FEATURE:
<223> OTHER INFORMATION: Synthetic DNA

<400> SEQUENCE: 58
gaaagtctgc ataattgcct                                                   20

<210> SEQ ID NO 59
<211> LENGTH: 51
<212> TYPE: DNA
<213> ORGANISM: Artificial sequence
<220> FEATURE:
<223> OTHER INFORMATION: Synthetic DNA

<400> SEQUENCE: 59
gagtcggtgc ttttttgaa ttctctagag tgtccgtgct gaatatccac c                  51

<210> SEQ ID NO 60
<211> LENGTH: 45
<212> TYPE: DNA
<213> ORGANISM: Artificial sequence
<220> FEATURE:
<223> OTHER INFORMATION: Synthetic DNA

<400> SEQUENCE: 60
atttacgacc tgcacagcca ttgctgctct ccttatcctt aatgg                        45

```
<210> SEQ ID NO 61
<211> LENGTH: 45
<212> TYPE: DNA
<213> ORGANISM: Artificial sequence
<220> FEATURE:
<223> OTHER INFORMATION: Synthetic DNA

<400> SEQUENCE: 61
ccattaagga taaggagagc agcaatggct gtgcaggtcg taaat            45

<210> SEQ ID NO 62
<211> LENGTH: 46
<212> TYPE: DNA
<213> ORGANISM: Artificial sequence
<220> FEATURE:
<223> OTHER INFORMATION: Synthetic DNA

<400> SEQUENCE: 62
cctgccaaaa ccggtaaaat gtatgtttgt agaaacgcaa aaaggc           46

<210> SEQ ID NO 63
<211> LENGTH: 46
<212> TYPE: DNA
<213> ORGANISM: Artificial sequence
<220> FEATURE:
<223> OTHER INFORMATION: Synthetic DNA

<400> SEQUENCE: 63 gccttttttgc gtttctacaa acatacattt taccggtttt ggcagg          46

<210> SEQ ID NO 64
<211> LENGTH: 50
<212> TYPE: DNA
<213> ORGANISM: Artificial sequence
<220> FEATURE:
<223> OTHER INFORMATION: Synthetic DNA

<400> SEQUENCE: 64
ggtaatagat ctaagcttct gcaggtcgac ccaccgcaa agatatgtcg         50

<210> SEQ ID NO 65
<211> LENGTH: 22
<212> TYPE: DNA
<213> ORGANISM: Artificial sequence
<220> FEATURE:
<223> OTHER INFORMATION: Synthetic DNA

<400> SEQUENCE: 65
gatattctgc cccagcactc ag                                     22

<210> SEQ ID NO 66
<211> LENGTH: 20
<212> TYPE: DNA
<213> ORGANISM: Artificial sequence
<220> FEATURE:
<223> OTHER INFORMATION: Synthetic DNA

<400> SEQUENCE: 66
gtgccacggt tagcctgtat                                        20
```

TYROSOL-PRODUCING RECOMBINANT ESCHERICHIA COLI AND CONSTRUCTION METHOD AND APPLICATION THEREOF

TECHNICAL FIELD

The disclosure relates to a tyrosol-producing recombinant *Escherichia coli* and a construction method and application thereof and belongs to the technical field of bioengineering.

BACKGROUND

Tyrosol is a phenolic compound with pharmacological activity, a derivative of phenethyl alcohol and a monophenolic antioxidant and has a variety of natural sources, such as olive oil and green tea. Tyrosol has many physiological active functions, such as an anti-oxidation function, an anti-fatigue function, an anti-anoxia function, an anti-stress function, an anti-cold function, a sedation function, a cardiovascular disease treatment function and a high blood pressure treatment function. Tyrosol can also be used as a flavoring agent for liquors and alcoholic beverages and plays an important role in enhancing the taste of alcoholic beverages, especially in sake, beer and wine. In addition, tyrosol is the precursor of 2-(3,4-dihydroxyphenyl)ethanol, which is an antioxidant beneficial to human health. Compared with tyrosol, 2-(3,4-dihydroxyphenyl)ethanol has a higher antioxidation property, and at the same time, 2-(3,4-dihydroxyphenyl)ethanol can also be used for synthesizing many polymers. Researches show that tyrosol has many biological properties and can be used for preventing cardiovascular diseases, osteohalsiteresis and other diseases. Therefore, tyrosol, as a fine chemical in the chemical industry and a biologically active compound in the pharmaceutical industry, has always attracted the attention of researchers.

Tyrosol synthesis methods mainly comprise plant extraction, chemical synthesis and biosynthesis. At present, the industrial production of tyrosol is mainly completed through chemical synthesis. This process has many drawbacks in subsequent extraction of tyrosol, and it is difficult to obtain high-purity tyrosol. It has been reported that the highest yield of tyrosol is 10.6 mM. Therefore, it is of great value to provide a high-yield production method of tyrosol for further application.

SUMMARY

The disclosure provides a recombinant *Escherichia coli*, five sites of a lacI site, a trpE site, a pabB site, a pabA site and a pykF site are deleted from an *E. coli* MG1655 genome, and at the same time, a *Saccharomyces cerevisiae* pyruvate decarboxylase gene ARO10* gene is integrated at each site of the five sites to obtain *Escherichia coli* YMGR5A.

The *Escherichia coli* YMGR5A is preserved at China Center for Type Culture Collection on May 24, 2019, the preservation number is CCTCC NO: M2019390, and the preservation address is Wuhan University, Wuhan, China.

In an embodiment of the disclosure, a nucleotide sequence of the ARO10* gene is shown as SEQ ID NO:1.

In an embodiment of the disclosure, a yccX site of the recombinant *Escherichia coli* is also deleted, and at the same time, the ARO10* gene is integrate at this site to obtain *Escherichia coli* YMGR6A (*E. coli* MG1655 ΔfeaB ΔpheA ΔtyrB lacI::ARO10* trpE::ARO10* pabB::ARO10* pabA::ARO10* pykF::ARO10* yccx::ARO10*).

The *Escherichia coli* YMGR6A is preserved at China Center for Type Culture Collection on May 24, 2019, the preservation number is CCTCC NO: M2019391, and the preservation address is Wuhan University, Wuhan, China.

In an embodiment of the disclosure, gene editing is carried out by using a CRISPR-cas9 technology or Red homologous recombination.

The disclosure provides a method for producing tyrosol, and the above recombinant *Escherichia coli* is used for fermentation.

In an embodiment of the disclosure, an M9Y culture medium is used for fermentation to produce tyrosol.

In an embodiment of the disclosure, the method comprises: subjecting strains to streak culture on a non-resistant LB plate, picking a single colony, inoculating a liquid LB culture medium the single colony, and culturing a seed solution for 8-10 hours.

In an embodiment of the disclosure, the method comprises: inoculating the liquid LB culture medium with the seed solution at an inoculation volume ratio of 1-5%, then placing in a 200-220 rpm shaker for culturing at 35-39° C. for 8-12 hours; collecting all cells, removing a supernatant after the cells are collected, and then cleaning the cells once with normal saline; and transferring the cleaned cells into the M9Y culture medium and then placing in the 200-220 rpm shaker for fermentation at 28-30° C. for 40-60 hours. Sampling is carried out every 12 hours.

In an embodiment of the disclosure, the method comprises: taking the seed solution, inoculating the liquid LB culture medium with the seed solution at the inoculation volume ratio of 1-5%, controlling an initial $OD_{600}$ to be 0.05-0.06, placing in the 200-220 rpm shaker for culturing at 35-39° C., and when the $OD_{600}$ reaches 0.25-0.30, inoculating a fermenter containing 40-45% of the M9Y culture medium with the seed solution. Glucose and yeast powder are added in the fermentation process.

In an embodiment of the disclosure, a formula of the M9Y culture medium comprises 17.1 g/L $Na_2HPO_4 \cdot 12H_2O$, 3 g/L $KH_2PO_4$, 0.5 g/L NaCl, 1 g/L $NH_4Cl$, 20 g/L glucose and 0.25 g/L yeast powder, and $MgSO_4$ is added at a final concentration of 5 mM after sterilization.

The disclosure provides a method for constructing the recombinant *Escherichia coli*, five sites of a lacI site, a trpE site, a pabB site, a pabA site and a pykF site are deleted from an *E. coli* MG1655 genome, at the same time, a *Saccharomyces cerevisiae* pyruvate decarboxylase gene ARO10* gene is integrated at each site of the five sites, and a nucleotide sequence of the ARO10* gene is shown as SEQ ID NO:1.

In an embodiment of the disclosure, a yccX site of the recombinant *Escherichia coli* is also deleted, and at the same time, the ARO10* gene is integrated at this site.

In an embodiment of the disclosure, gene editing is carried out by using a CRISPR-cas9 technology or Red homologous recombination.

The disclosure provides application of the recombinant *Escherichia coli* in the fields of food, chemical engineering or pharmacy.

The disclosure provides application of the method for producing tyrosol in the fields of food, chemical engineering or pharmacy.

Beneficial Effects of the Disclosure

The disclosure constructs a strain with high-yield production of tyrosol, the five sites of the lacI site, the trpE site, the pabB site, the pabA site and the pykF site of the *Escherichia coli* genome are deleted, and at the same time, the ARO10* gene is integrated at each site of the five sites to obtain a strain containing multiple copies of the ARO10* gene. On the basis of the recombinant strain, the ARO10* gene is randomly integrated at multiple sites, and it is found that the strain with high-yield production of tyrosol can be obtained by inserting the ARO10* gene at the yccX site. Fermentation using this strain does not require inducers or antibiotics. After fermentation is carried out for 48 hours, the yield of tyrosol can reach 32.3 mM.

Preservation of Biological Materials

An *Escherichia coli*, classified and named as *Escherichia coli* YMGR5A, is preserved at China Center for Type Culture Collection on May 24, 2019, the preservation number is CCTCC NO: M2019390, and the preservation address is Wuhan University, Wuhan, China.

An *Escherichia coli*, classified and named as *Escherichia coli* YMGR6A, is preserved at China Center for Type Culture Collection on May 24, 2019, the preservation number is CCTCC NO: M2019391, and the preservation address is Wuhan University, Wuhan, China.

DETAILED DESCRIPTION

Figure 1:
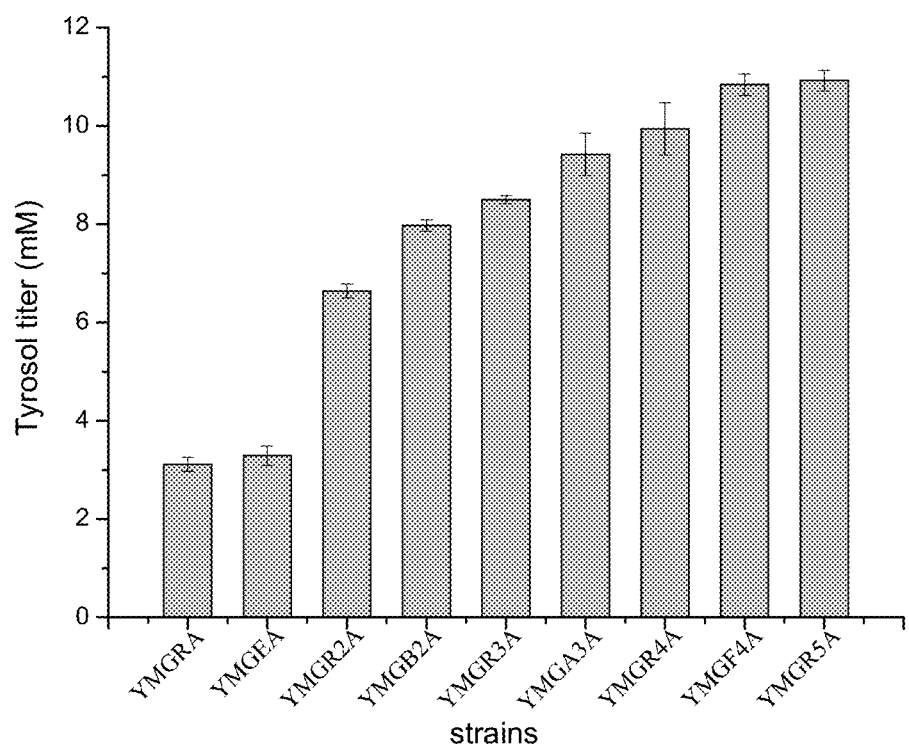
FIG. 1: The yield result of fermented tyrosol of 9 strains (YMGRA; YMGEA, YMGR2A; YMGB2A, YMGR3A; YMGA3A, YMGR4A; YMGF4A, YMGR5A) constructed in the disclosure.

I. High Performance Liquid Chromatography (HPLC) is Used for Detecting the Yield of Tyrosol Specific chromatographic detection conditions are as follows: An Agela Innoval C18 chromatographic column (4.6*250 mm, pore size 5 μm); a mobile phase comprising 0.1% formic acid (80%) and methanol (20%); flow rate: 1 mL·min$^{-1}$; sample injection volume: 10 μL; a UV detector, detection wavelength: 276 nm; and column temperature: 30° C.

II. Culture Mediums

An M9Y culture medium: 17.1 g/L $Na_2HPO_4.12H_2O$, 3 g/L $KH_2PO_4$, 0.5 g/L NaCl, 1 g/L $NH_4Cl$, 20 g/L glucose and 0.25 g/L yeast powder; and $MgSO_4$ is added at a final concentration of 5 mM after sterilization.

An LB culture medium: 10 g/L tryptone, 5 g/L yeast extract, and 10 g/L NaCl.

Example 1 Heterologous Expression of a *Saccharomyces cerevisiae* Pyruvate Decarboxylase Gene in *Escherichia coli* MG1655 to Produce Tyrosol I. Construction of a Plasmid pKK223-3-ARO10*

A codon-optimized ARO10* gene sequence is chemically synthesized by Suzhou Hongxun Biotechnologies CO., LTD. The synthesized gene sequence is inserted into the EcoR I and Hind III sites of a plasmid pKK223-3 to obtain a recombinant plasmid pKK223-3-ARO10*.

II. Construction of a lacI::ARO10* Deletion Expression Cassette

The plasmid pKK223-3 is used as a template, designed primers ARO10-L and LacIR (Table 1) are used for amplification to obtain an expression fragment of tac-ARO10*-rrnB with a promoter and a terminator, and the expression fragment is inserted into a pMD19-T simple plasmid to obtain a recombinant plasmid 19Ts-tac-ARO10*-rrnB. Primers LacIL and PKDR are designed, and pKD13 is used as a template for amplification to obtain a Kana resistant fragment. The plasmid 19Ts-tac-ARO10*-rrnB and the Kana resistant fragment are subjected to enzyme digestion and ligation with Xho I to obtain a recombinant plasmid 19Ts-Kana-tac-ARO10*-rrnB. The constructed plasmid 19Ts-Kana-tac-ARO10*-rrnB is used as a template, and lacIL and lacIR are used as primers for PCR amplification to obtain a lacI::ARO10* deletion expression cassette.

TABLE 1

Primers

| Primer name | Sequence (5'-3') | Sequence |
|---|---|---|
| ARO10-L | GGCTCGAGATGGCTGTGCAGGTCGTAAAT | SEQ ID NO: 2 |
| IacIR | GGGGTACCGTGAAACCAGTAACGTTATACGATG TCGCAGAGTTCA TCACTGCCCGCTTTCCAGTCGGGAAACCTGTCG TGCCAGCTGCATTAATGAATCGGCCAACGCGCG GGGAGAAGAGTTTGTAGAAACGC | SEQ ID NO: 3 |
| LacIL | CCCTCGAGGTGAAACCAGTAACGTTATACGATG TCGCAGAGTATGCCGGTGTCTCTTATCAGACCG TTTGTGTAGGCTGGAGCTGCTTC | SEQ ID NO: 4 |
| PKDR | CCCTCGAGattccggggatccgtcgacc | SEQ ID NO: 5 |
| YLACIL | GAAGCGGCATGCATTTACGT | SEQ ID NO: 6 |
| YLACIR | ACAACATACGAGCCGGAAGC | SEQ ID NO: 7 |
| pTarget-R | CGGACTAGTATTATACCTAGGACTGAGC | SEQ ID NO: 8 |
| sg-trpE | CGGACTAGTCCTGTTCTCTTATGACCTTGGTTTT AGAGCTAGAAATAGC | SEQ ID NO: 9 |
| sg-trpE-test | CCTGTTCTCTTATGACCTTG | SEQ ID NO: 10 |
| 700trpE-U-L | gagtcggtgctttttttgaattctctagaCCAGGT ATTTGCGCTTTTTCAAGTC | SEQ ID NO: 11 |

TABLE 1-continued

Primers

| Primer name | Sequence (5'-3') | Sequence |
|---|---|---|
| 700trpE-U-R | ATTTACGACCTGCACAGCCATCGGGCTGGGTATCTGATTGCTT | SEQ ID NO: 12 |
| trpE-ARO10-L | AAGCAATCAGATACCCAGCCCGatggctgtgcaggtcgtaaat | SEQ ID NO: 13 |
| trpE-ARO10-R | GAATGTCAGCCATCAGAAAGTCTCCGTTTGTAGAAACGCAAAAGGC | SEQ ID NO: 14 |
| 700trpE-D-L | gccttttgcgtttctacaaacGGAGACTTTCTGATGGCTGACATTC | SEQ ID NO: 15 |
| 700trpE-D-R | GGTAATAGATCTAAGCTTCTGCAGGTCGACGCTGAAAACAGCTGGTGGCT TTC | SEQ ID NO: 16 |
| 500trpE-U-L | CCAGACCGTGGAAATTTCCACG | SEQ ID NO: 17 |
| 500trpE-D-R | GAGAATGGATTCCGGATGGAACTGG | SEQ ID NO: 18 |
| ΔtrpE-U-R | GAATGTCAGCCATCAGAAAGTCTCCCGGGCTGGGTATCTGATTGCTT | SEQ ID NO: 19 |
| ΔtrpE-D-L | AAGCAATCAGATACCCAGCCCGGGAGACTTTCTGATGGCTGACATTC | SEQ ID NO: 20 |
| sg-pabB | GTCCTAGGTATAATACTAGTTAACCGGGGCTCCGAAAGTAGITTIAGAGCTAGAAATAGC | SEQ ID NO: 21 |
| sg-pabB-test | TAACCGGGGCTCCGAAAGTA | SEQ ID NO: 22 |
| 700pabB-U-L | gagtcggtgcttttttttgaattctctagaCCCTGGATTTCATTGGTGCC | SEQ ID NO: 23 |
| 700pabB-U-R | ATTTACGACCTGCACAGCCATCAGTCCTGACTCTACTGGCTATGTG | SEQ ID NO: 24 |
| pabB-ARO10-L | CACATAGCCAGTAGAGTCAGGACTGatggctgtgcaggtcgtaaat | SEQ ID NO: 25 |
| pabB-ARO10-R | AGGCTACGGTATTCCACGTCGTTTGTAGAAACGCAAAAGGC | SEQ ID NO: 26 |
| 700pabB-D-L | gccttttgcgtttctacaaacGACGTGGAATACCGCTAGCT | SEQ ID NO: 27 |
| 700pabB-D-R | GGTAATAGATCTAAGCTTCTGCAGGTCGACCACGAATTATGCCTGCGGTC | SEQ ID NO: 28 |
| 500pabB-U-L | GCCTGCTGTAATAGATAAAGCC | SEQ ID NO: 29 |
| 500pabB-D-R | GGCGACTGGC TTAACTATTCAC | SEQ ID NO: 30 |
| ΔpabB-U-R | CAGGCTACGGTATTCCACGTCCAGTCCTGACTCTACTGGCTATG | SEQ ID NO: 31 |
| ΔpabB-D-L | CATAGCCAGTAGAGTCAGGACTGGACGTGGAATACCGTAGCCTG | SEQ ID NO: 32 |
| sg-pabA | GTCCTAGGTATAATACTAGTACGTTATTCGCCACTATGCCGTTTTAGAGCTAGAAATAGC | SEQ ID NO: 33 |
| sg-pabA-test | ACGTTATTCGCCACTATGCC | SEQ ID NO: 34 |
| 700pabA-U-L | gagtcggtgcttttttttgaattctctagaGCCTTTAGTCACTCTTACTGCCGC | SEQ ID NO: 35 |
| 700pabA-U-R | ATTTACGACCTGCACAGCCATGGCGGCTCCGGTACAAAAGAAC | SEQ ID NO: 36 |
| pabA-ARO10-L | GTTCTTTIGIACCGGAGCCGCCATGGCTGTGCAGGTCGTAAAT | SEQ ID NO: 37 |
| pabA-ARO10-R | GATCACCCTGTTACGCATAAACGTTTGTAGAAACGCAAAAGGC | SEQ ID NO: 38 |
| 700pabA-D-L | gccttttgcgtttctacaaacGTTTATGCGTAACAGGGTGATC | SEQ ID NO: 39 |

TABLE 1-continued

Primers

| Primer name | Sequence (5'-3') | Sequence |
|---|---|---|
| 700pabA-D-R | GGTAATAGATCTAAGCTTCTGCAGGTCGACTGG ATCGGCTCAACCACCA | SEQ ID NO: 40 |
| 500pabA-U-L | GACCATTGAGCTTGGTCCGC | SEQ ID NO: 41 |
| 500pabA-D-R | CCACCCACCGAAACGGTAAAC | SEQ ID NO: 42 |
| ΔpabA-U-R | GATCACCCTGTTACGCATAAACGGCGGCTCCGG TACAAAGAAC | SEQ ID NO: 43 |
| ΔpabA-D-L | GTTCTTTTGTACCGGAGCCGCCGTTTATGCGTA ACAGGGTGATC | SEQ ID NO: 44 |
| sg-pykF | GTCCTAGGTATAATACTAGTATGGTTGCGGTAAC GTATGAGTTTTAGAGCTAGAAATAGC | SEQ ID NO: 45 |
| sg-pykF-test | ATGGTTGCGGTAACGTATGA | SEQ ID NO: 46 |
| 700pykF-U-L | gagtcggtgctttttttgaattctctagaGGCT AATGCTGTACGTAATACGC | SEQ ID NO: 47 |
| 700pykF-U-R | ATTTACGACC TGCACAGCCA TGTTGAGAAG GATGGGAGAAAC | SEQ ID NO: 48 |
| pykF-ARO10-L | GTTTCTCCCATCCTTCTCAACATGGCTGTGCAGG TCGTAAAT | SEQ ID NO: 49 |
| pykF-ARO10-R | CATCAGGGCGCTTCGATATACGTTTGTAGAAAC GCAAAAAGGC | SEQ ID NO: 50 |
| 700pykF-D-L | gccttttttgcgtttctacaaacGTATA TCGAAGCGCC CTGATG | SEQ ID NO: 51 |
| 700pykF-D-R | GGTAATAGATCTAAGCTTCTGCAGGTCGACCAG CAATGCGCCTTCAGTAG | SEQ ID NO: 52 |
| 500pykF-U-L | CTGCACATTTCTCGGTACAGTTC | SEQ ID NO: 53 |
| 500pykF-D-R | CGCACAATGTGCGCCATTT | SEQ ID NO: 54 |
| ΔpykF-U-R | GTTTCTCCCATCCTTCTCAACGTATATCGAAGCG CCCTGATG | SEQ ID NO: 55 |
| ΔpykF-D-L | CATCAGGGCGCTTCGATATACGTTGAGAAGGAT GGGAGAAAC | SEQ ID NO: 56 |
| sg-yccx | GTCCTAGGTATAATACTAGTGAAAGTCTGCATAA TTGCCTGTTTTAGAGCTAGAAATAGC | SEQ ID NO: 57 |
| sg-yccx-test | GAAAGTCTGCATAATTGCCT | SEQ ID NO: 58 |
| 700yccx-U-L | gagtcggtgctttttttgaattctctagaGTGTCC GTGCTGAATATCCACC | SEQ ID NO: 59 |
| 700pykF-U-R | ATTTACGACCTGCACAGCCA TTGCTGCTCT CCTTATCCTTAATGG | SEQ ID NO: 60 |
| yccx-ARO10-L | ccattaaggataaggagagcagcaATGGCTGTGCAGG TCGTAAAT | SEQ ID NO: 61 |
| yccx-ARO10-R | CCTGCCAAAACCGGTAAAATGTATGTTTGT AGAAACGCAAAAAGGC | SEQ ID NO: 62 |
| 700yccx-D-L | gccttttttgcgtttctacaaacATACATTTTAC CGGTTTTGGCAGG | SEQ ID NO: 63 |
| 700yccx-D-R | GGTAATAGATCTAAGCTTCTGCAGGTCGACCCA CCCGCAAAGATATGTCG | SEQ ID NO: 64 |
| 500yccx-U-L | GATATTCTGC CCCAGCACTCAG | SEQ ID NO: 65 |
| 500yccx-D-R | GTGCCACGGT TAGCCTGTAT | SEQ ID NO: 66 |

III. Construction of a Strain YMGRA (*E. coli* MG1655 ΔfeaB ΔpheA ΔtyrB ΔtyrR lacI:ARO10*)

A Red homologous recombination method is adopted, YMGR/pKD46 (*E. coli* MG1655 ΔfeaB ΔpheA ΔtyrB ΔtyrR/pKD46) is prepared into a competent cell, and the previously constructed lacI:ARO10* deletion expression cassette is transferred into the competent cell. A transformant is picked, colony PCR is carried out with primers YLACIL and YLACIR to verify the transformation situation, and the strain YMGR/pKD46 is used as a contrast. A plasmid pCP20 is transferred into the strain YMGR/pKD46 to eliminate kanamycin resistance. The high temperature of 42° C. is used for eliminating the plasmids pKD46 and pCP20. A strain YMGRA is obtained.

Example 2 Construction of a Strain YMGEA (*E. coli* MG1655 ΔfeaB ΔpheA ΔtyrB ΔtyrR ΔtrpE lacI:ARO10* trpE) and a Strain YMGR2A (*E. coli* MG1655 ΔfeaB ΔpheA ΔtyrB ΔtyrR lacI:ARO10* trpE::ARO10*)

I. Construction of a trpE Deletion Cassette and a trpE::ARO10* Deletion Expression Cassette Primers 700trpE-U-L, ΔtrpE-U-R, ΔtrpE-D-L and 700trpE-D-R are designed according to the gene sequence of trpE, an *E. coli* MG1655 genome is used as a template, and fragments DtrpEUP and DtrpEDown are obtained through respective PCR amplification. 500trpE-U-L and 500trpE-D-R are used as primers, and a nested PCR method is adopted for amplification to obtain a gene trpE deletion cassette. Primers 700trpE-U-L, 700trpE-U-R, trpE-ARO10-L, trpE-ARO10-R, 700trpE-D-L and 700trpE-D-R are designed according to the gene sequence of trpE and a plasmid pKK223-ARO10*; the *E. coli* MG1655 genome and the plasmid pKK223-ARO10* are used as templates respectively for amplification to obtain fragments trpEUP, trpEDown, and ARO10. A plasmid pTarget is subjected to enzyme digestion with Xba I, and fragments are recovered. The four fragments are ligated by using a Vazyme one-step cloning kit to obtain a correct plasmid, and 500trpE-U-L and 500trpE-D-R are used as primers for PCR amplification to obtain a trpE::ARO10* deletion expression cassette.

II. Construction of a Strain YMGEA (*E. coli* MG1655 ΔfeaB ΔpheA ΔtyrB ΔtyrR ΔtrpE lacI:ARO10* trpE) and a Strain YMGR2A (*E. coli* MG1655 ΔfeaB ΔpheA ΔtyrB ΔtyrR lacI:ARO10* trpE::ARO10*)

The CRISPR-cas9 method is adopted for preparing a YMGRA/pCas (*E. coli* MG1655 ΔfeaB ΔpheA ΔtyrB ΔtyrR lacI:ARO10*/pCas) competent cell, and a sgRNA-containing plasmid sg-pTarget-trpE and the above trpE deletion cassette are transferred into the competent cell. A transformant is picked, colony PCR verification is carried out with primers 700trpE-U-L and 700trpE-D-R, and the strain YMGRA/pCas is used as a contrast. IPTG is adopted for induction, the plasmid sg-pTarget-trpE is eliminated, the high temperature of 42° C. is used for eliminating the plasmid pCas, and a strain YMGEA is obtained.

The sgRNA-containing plasmid sg-pTarget-trpE and the trpE::ARO10* deletion cassette are transferred into the competent cell. A transformant is picked, colony PCR verification is carried out with primers 700trpE-U-L and 700trpE-D-R, and the strain YMGRA/pCas is used as a contrast. IPTG is adopted for induction, the plasmid sg-pTarget-trpE is eliminated, the high temperature of 42° C. is used for eliminating the plasmid pCas, and a strain YMGR2A is obtained.

Example 3 Construction of a Strain YMGB2A (*E. coli* MG1655 ΔfeaB ΔpheA ΔtyrB ΔtyrR ΔpabB lacI:ARO10* trpE::ARO10*) and a Strain YMGR3A (*E. coli* MG1655 ΔfeaB ΔpheA ΔtyrB ΔtyrR lacI:ARO10* trpE::ARO10* pabB::ARO10*)

A pabB deletion cassette and a pabB::ARO10* deletion expression cassette are constructed by using the strategy same as the construction of the deletion cassette and the trpE::ARO10* deletion expression cassette, YMGR2A/pCas is prepared into a competent cell by using the CRISPR-cas9 method, and a sgRNA-containing plasmid sg-pTarget-pabB and the constructed pabB deletion cassette are transferred into the competent cell for transformation. A transformant is picked, colony PCR verification is carried out with primers 700pabB-U-L and 700pabB-D-R, and the strain YMGR2A/pCas is used as a contrast. IPTG is adopted for induction, the plasmid sg-pTarget-pabB is eliminated, the high temperature of 42° C. is used for eliminating the plasmid pCas, the method is similar to that of Example 2, and a strain YMGB2A is obtained.

YMGR2A/pCas is prepared into the competent cell by using the CRISPR-cas9 method, and the sgRNA-containing plasmid sg-pTarget-pabB and the constructed pabB::ARO10* deletion expression cassette are added into the competent cell for transformation. A transformant is picked, colony PCR verification is carried out with primers 700pabB-U-L and 700pabB-D-R, and the strain YMGR2A/pCas is used as a contrast. IPTG is adopted for induction, the plasmid sg-pTarget-pabB is eliminated, the high temperature of 42° C. is used for eliminating the plasmid pCas, the method is similar to that of Example 2, and a strain YMGR3A is obtained.

Example 4 Construction of a Strain YMGA3A (*E. coli* MG1655 ΔfeaB ΔpheA ΔtyrB ΔtyrR ΔpabA lacI:ARO10* trpE::ARO10* pabB::ARO101 and a Strain YMGR4A (*E. coli* MG1655 ΔfeaB ΔpheA ΔtyrB ΔtyrR lacI:ARO10* trpE::ARO10* pabB::ARO10* pabA::ARO10*)

A pabA deletion cassette and a pabA::ARO10* deletion expression cassette are constructed by using the strategy same as the construction of the trpE deletion cassette and the trpE::ARO10* deletion expression cassette, YMGR3A/pCas is prepared into an electrocompetent cell by using the CRISPR-cas9 method, and a sgRNA-containing plasmid sg-pTarget-pabA and the above pabA deletion cassette or the pabA::ARO10* deletion expression cassette are added into the competent cell for transformation. A transformant is picked, colony PCR verification is carried out with primers 700pabA-U-L and 700pabA-D-R, and the strain YMGR3A/pCas is used as a contrast. IPTG is adopted for induction, the plasmid sg-pTarget-pabA is eliminated, the high temperature of 42° C. is used for eliminating the plasmid pCas, and the method is similar to that of Example 2. Strains YMGA3A and YMGR4A are obtained.

Example 5 Construction of a Strain YMGF4A (*E. coli* MG1655 ΔfeaB ΔpheA ΔtyrB ΔtyrR ΔpykF lacI:ARO10* trpE::ARO10* pabB::ARO10* pabA::ARO10*) and a Strain YMGR5A (*E. coli* MG1655 ΔfeaB ΔpheA ΔtyrB ΔtyrR lacI:ARO10* trpE::ARO10* pabB::ARO10* pabA::ARO10* pykF::ARO10*)

A pykF deletion cassette and a pykF::ARO10* deletion expression cassette are constructed by using the strategy same as the construction of the trpE deletion cassette and the trpE::ARO10* deletion expression cassette, YMGR4A/pCas is prepared into a competent cell by using the CRISPR-cas9 method, and a sgRNA-containing plasmid sg-pTarget-pykF and the above pykF deletion cassette or the pykF::ARO10* deletion expression cassette are added into the competent cell for transformation. A transformant is picked, colony PCR verification is carried out with primers 700pykF-U-L and 700pykF-D-R, and the strain YMGR4A/pCas is used as a contrast. IPTG is adopted for induction, the plasmid sg-pTarget-pykF is eliminated, the high temperature of 42° C. is used for eliminating the plasmid pCas, and the method is similar to that of Example 2. Strains YMGF4A and YMGR5A are obtained.

Figure 2:
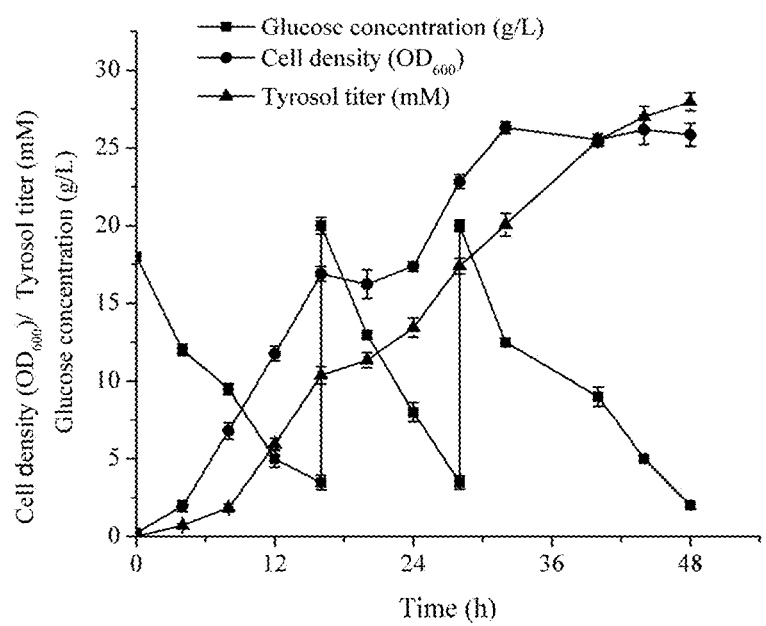
FIG. 2: The yield result of fermented tyrosol of YMGR5A constructed in the disclosure in a fermenter.

Example 6 Shake Flask Fermentation of Microorganisms for Synthetizing Tyrosol Strains are subjected to streak culture on a non-resistant LB plate, a single colony is picked, 20 mL of a liquid LB culture medium is inoculated with the single colony, and a seed solution is cultured for 8-10 hours. 500 µL of the seed solution is taken, and 50 mL of a liquid LB culture medium is inoculated with the 500 µL of the seed solution for expanded culture, and then placed in a 200 r·min$^{-1}$ shaker for culturing at 37° C. for 10 hours. All cells are collected, a supernatant is removed after the cells are collected, and then the cells are cleaned once with normal saline. The cleaned cells are transferred into 50 mL of M9Y fermentation culture medium to make the cell density in the culture medium reach 6*10$^9$ CFU/mL when the OD$_{600}$ is about 5, and the cells are fermented in the 200 r·min$^{-1}$ shaker at 30° C. for 48 hours. Sampling is carried out every 12 hours. High performance liquid chromatography (HPLC) is used for detecting the yield of tyrosol. The yield result of tyrosol is shown as FIG. 1 and Table 2. The yield of tyrosol is gradually increased by knocking out relevant genes of competition pathways and appropriately increasing the copy number of the ARO10* gene. When the pykF gene is knocked out, the yield of tyrosol reaches 10.84. mM. When the pykF gene is knocked out and the ARO10* gene is integrated, the yield of tyrosol reaches 10.92 mM. It can be seen that continuous increase of the ARO10* gene has little effect on the yield of tyrosol.

inoculated with the seed solution, sampling is carried out every 4 hours, and appropriate amounts of glucose and yeast powder are added. High performance liquid chromatography (HPLC) is used for detecting the yield of tyrosol. The yield result of tyrosol is shown as FIG. 2. When fermentation is carried out for 48 hours, the yield of tyrosol in the fermenter reaches 27.96 mM.

Example 8 Construction of a Strain YMGR6A (*E. coli* MG1655 ΔfeaB ΔpheA ΔtyrB ΔtyrR lacI::ARO10* trpE::ARO10* pabB::ARO10* pabA::ARO10* pykF::ARO10* yccx::ARO10*)

A yccx::ARO10* deletion expression cassette is constructed by using the expression strategy same as the construction of the trpE::ARO10* deletion expression cassette, YMGR5A/pCas is prepared into a competent cell by using the CRISPR-cas9 method, and a sgRNA-containing plasmid sg-pTarget-yccx and the yccx::ARO10* deletion expression cassette are added into the competent cell for transformation. A transformant is picked, colony PCR verification is carried out with primers 700yccx-U-L and 700yccx-D-R, and the strain YMGR5A/pCas is used as a contrast. IPTG is adopted for induction, the plasmid sg-pTarget-yccx is eliminated, the high temperature of 42° C. is used for eliminating the plasmid pCas, and the method is similar to that of Example 2. A strain YMGR6A is obtained, the yield of tyrosol obtained after shake flask fermentation reaches 11.74 mM, and the fermentation method is the same as that of Example 6.

Culture in a fermenter to produce tyrosol: YMGR6A is subjected to streak culture on an LB plate, a single colony is picked, and 20 mL of a liquid LB culture medium is inoculated with the single colony, and a seed solution is cultured for 8-10 hours. The seed solution is taken, 50 mL of a liquid LB culture medium is inoculated with the seed solution, the initial OD$_{600}$ is controlled to be 0.05, and the liquid LB culture medium inoculated with the seed solution is placed in a 200 r·min$^{-1}$ shaker for expanded culture at 37° C. for 5 hours. When the OD$_{600}$ reaches 0.25, a 5 L fermenter containing 2 L of an M9Y culture medium is inoculated with the seed solution, sampling is carried out

TABLE 2

The yield of tyrosol obtained by fermenting different strains

| Strains | YMGRA | YMGEA | YMGR2A | YMGB2A | YMGR3A | YMGA3A | YMGR4A | YMGF4A | YMGR5A |
|---|---|---|---|---|---|---|---|---|---|
| Yield of tyrosol (mM) | 3.11 | 3.29 | 6.64 | 7.97 | 8.5 | 9.42 | 9.94 | 10.84 | 10.92 |

Example 7 Culture of YMGR5A in a Fermenter to Produce Tyrosol

Figure 3:
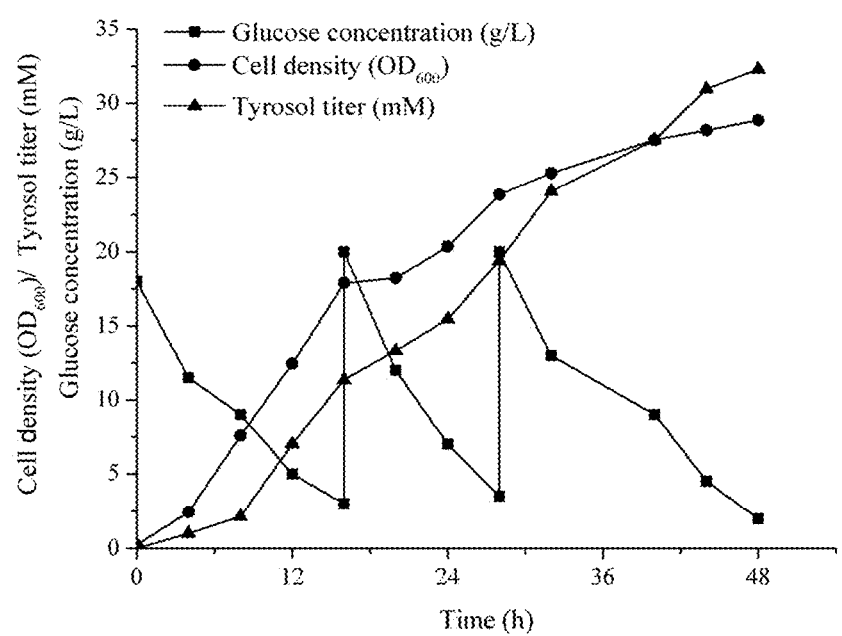
FIG. 3: The yield result of fermented tyrosol of YMGR6A constructed in the disclosure in a fermenter.

YMGR5A is subjected to streak culture on an LB plate, a single colony is picked, 20 mL liquid LB culture medium is inoculated with the single colony, and a seed solution is cultured for 8-10 hours. The seed solution is taken, a 50 mL liquid LB culture medium is inoculated with the seed solution, the initial OD$_{600}$ is controlled to be 0.05, and the liquid LB culture medium inoculated with the seed solution is placed in a 200 r·min$^{-1}$ shaker for expanded culture at 37° C. for 5 hours. When the OD$_{600}$ reaches 0.25, a 5 L fermenter containing 2 L of an M9Y culture medium is every 4 hours, and appropriate amounts of glucose and yeast powder are added. High performance liquid chromatography (HPLC) is used for detecting the yield of tyrosol. The yield result of tyrosol is shown as FIG. 3. When fermentation is carried out for 48 hours, the yield of tyrosol reaches 32.3 mM.

Although the present disclosure has been disclosed as above as exemplary examples, it is not intended to limit the present disclosure. Any of those skilled in the art may make various alterations and modifications without departing from the spirit and scope of the present disclosure. Therefore, the protection scope of the present disclosure shall be as defined in the claims.

What is claimed is:

1. A recombinant *Escherichia coli* obtained by (i) introducing deletions in *E. coli* MG1655 at a lacI gene, a trpE gene, a pabB gene, a pabA gene, and a pykF gene, and (ii) integrating a *Saccharomyces cerevisiae* pyruvate decarboxylase ARO10* gene that comprises SEQ ID NO:1 in each of the lacI gene, trpE gene, pabB gene, pabA gene, and pykF gene having said deletions.

2. The recombinant *Escherichia coli* according to claim 1, wherein a yccX gene in said recombinant *Escherichia coli* is also deleted, and at the same time a *Saccharomyces cerevisiae* pyruvate decarboxylase ARO10* gene that comprises SEQ ID NO:1 is integrated in the yccX gene having said deletion.

3. The recombinant *Escherichia coli* according to claim 2, wherein deletion or gene integration is carried out by using CRISPR-Cas9 technology or Red homologous recombination.

4. A method for producing a tyrosol, wherein said method comprises fermenting the recombinant *Escherichia coli* according to claim 1.

5. The method according to claim 4, wherein an M9Y culture medium is used as a fermentation culture medium.

6. The method according to claim 4, wherein prior to fermenting, the method comprises (a) culturing the recombinant *Escherichia coli* on an LB plate, (b) selecting a single colony from said LB plate, (c) inoculating an LB liquid culture medium with said single colony, and (d) culturing said single colony for 8-10 hours to produce a seed solution.

7. The method according to claim 6, wherein said method further comprises inoculating an LB liquid solution with the seed solution at an inoculation volume percentage of 1%-5%, culturing said inoculated LB liquid solution in a shaker at 200-220 rpm for 8-12 hours at 35° C.-39° C., collecting all cells after culturing, removing the culture medium from the cells, cleaning the cells after removing the cell culture medium, transferring the clean cells into an M9Y medium, and culturing the cells in the M9Y medium in a shaker at 200-220 rpm for 40-60 hours at 28° C.-30° C.

8. The method according to claim 6, wherein said method further comprises inoculating an LB liquid solution with the seed solution at an inoculation volume percentage of 1%-5% to obtain an initial $OD_{600}$ of 0.05-0.06, culturing said inoculated LB liquid solution in a shaker at 200-220 rpm at 35° C.-39° C. until the $OD_{600}$ reaches 0.25-0.30 to obtain a fermentation seed solution, inoculating a fermenter that comprises a M9Y medium with the fermentation seed solution, and fermenting for 40-60 hours.

9. The method according to claim 8, wherein the M9Y medium comprises 17.1 g/L $Na_2HPO_4.12H_2O$, 3 g/L $KH_2PO_4$, 0.5 g/L NaCl, 1 g/L $NH_4Cl$, 20 g/L glucose, 0.25 g/L yeast powder and 5 mM $MgSO_4$, wherein $MgSO_4$ is added after sterilization.

10. The method according to claim 4, wherein the tyrosol produced is used to prepare food or medicine.

11. A method for constructing a recombinant *Escherichia coli*, wherein said method comprises (i) introducing deletions in an *E. coli* MG1655 cell at a lacI gene, a trpE gene, a pabB gene, a pabA gene, and a pykF gene, and (ii) integrating a *Saccharomyces cerevisiae* pyruvate decarboxylase ARO10* gene that comprises SEQ ID NO:1 in each of the lacI gene, trpE gene, pabB gene, pabA gene, and pykF gene having said deletions.

12. The method according to claim 11, wherein said method further comprises introducing a deletion in said *E. coli* MG1655 cell at a yccX gene, and at the same time integrating a *Saccharomyces cerevisiae* pyruvate decarboxylase ARO10* gene that comprises SEQ ID NO:1 in the yccX gene having said deletion.

13. The method according to claim 11, wherein deletion or gene integration is carried out by using CRISPR-Cas9 technology or Red homologous recombination.

* * * * *